United States Patent [19]

Austin

[11] 4,427,654

[45] Jan. 24, 1984

[54] WOUND HEALING COMPOSITIONS AND FORMULATIONS

[75] Inventor: Paul R. Austin, Wilmington, Del.

[73] Assignee: University of Delaware, Newark, Del.

[21] Appl. No.: 402,296

[22] Filed: Jul. 27, 1982

[51] Int. Cl.³ .............................................. A61K 35/56
[52] U.S. Cl. ..................................................... 424/95
[58] Field of Search ........................................... 424/95

[56] References Cited

PUBLICATIONS

Hackman–Australian J. of Biological Sciences, vol. 13, No. 4, (1960), p. 568.
Giles et al.–Chem. Abst., vol. 71, (1969), p. 56801v.
Hunt et al.–Chem. Abst., vol. 95, (1981), p. 39362f.

*Primary Examiner*—Sam Rosen

[57] ABSTRACT

Wound healing compositions and formulations containing same are described, as well as the use of such compositions and formulations. The compositions are finely divided cephalopod skeletons, particularly those from cuttlefish and squid. The formulations include such compositions in a compatible carrier.

8 Claims, No Drawings

WOUND HEALING COMPOSITIONS AND FORMULATIONS

The invention relates to wound healing compositions and formulations containing same.

Some agents which promote the healing of wounds in mammalian bodies are known. Prudden, J. F. and Allen, J. (J. Am. Med. Assn., Vol. 192, pp. 352-356; (1965) have shown that modified animal cartilage promotes the healing of wounds in humans. Carlozzi et al. (U.S. Pat. No. 3,232,836; 1966) have shown that N-acetyl glucosamine and related compounds facilitate the healing of body wounds in humans and animals. Balassa (U.S. Pat. No. 3,632,754; 1972) has shown that finely divided chitin, partially depolymerized chitin, and chitin derivatives promote the healing of wounds.

Since the art shows that improved rates of wound healing are obtainable, the search for agents with improved wound healing properties has continued, particularly in view of certain limitations and objectionable features. For example, each requires considerable chemical processing, enzymatic digestion or other manipulation, and the products are artifacts, rather than natural substances.

It has now been discovered that finely divided cephalopod skeletons, when topically applied, e.g., applied externally especially in a compatible carrier, to mammalian wounds, show improved effectiveness in promoting healing of the wounds. By "promoting healing" I mean that the treated wound is healed more rapidly and/or that the healed bond has greater resistance to physical rupture than an otherwise similar but untreated wound. Other features noted at times with the use of the products of this invention are the alleviation of pain, itching or other irritation. The products of the invention are applicable to abrasions, scratches, chapped skin, bed sores, cuts, burns, and hemorrhoids.

While all cephalopod skeletons are believed operable in this invention, the most readily available, and therefore preferred, are those from cuttlefish (cuttlebone) and squid (squid pen). Of these, cuttlebone is commercially available as a bird feed and squid pen can be readily isolated and purified from wastes in processing squid for food.

One method of isolating cephalopod skeletons involves boiling the wastes in water, mechanically separating the skeleton structures and then treating them by scrubbing, by ultrasonic vibration, or with detergents to remove adventitious protein. The dried skeletons are then ground to a fine powder.

Cephalopod skeletons, particularly cuttlebone, differ from crustacean shells in that they are substantially less calcified and much easier to grind.

The ground cephalopod skeletal material may be dusted directly on the wound or may be applied by a compatible carrier. The carrier in which the ground cephalopod skeletal material is applied to a wound may comprise any of the means commonly used to maintain a medicament in contact with a wound. The carrier may be a gas, liquid or solid. For example, the ground cephalopod skeletal powder may be dusted between the fibers of a gauze pad and applied as a dressing to a wound. Also, the powder may be suspended in a liquid or wax or fatty carrier and applied to the wound as an ointment or salve.

In the examples which follow, six representative formulations containing cephalopod skeleton powders were employed.

FORMULATION 1

Commerical cuttlebone (Geisler Pet Products, Inc., Fairfield, NJ, 07006) ground to 120 mesh (125 microns) was placed in a high-torque mechanical stirrer with five times its weight of a commercial skin dressing containing water, cetyl alcohol, glyceryl stearate, mineral oil, glycerine, stearic acid, triethanolamine, dimethicon FEG-40 (dimethyl polysiloxane), sorbitan lanolate, methyl paraben, Quaternium 15 and propyl paraben (marketed as "Rose Milk" by Century Creations, Inc., Venice, CA 90271). The mixture was stirred at high speed until homogenized. The paste-like product was stored in salve jars for use. Paraben is para-hydroxybenzoic acid.

FORMULATION 2

The procedure of Formulation 1 was repeated except that the commercial skin dressing contained water, mineral oil, potassium stearate, sodium stearate, cholesterol, cetyl palmitate, butyl paraben, sodium carbomer, potassium carbomer 934, propyl paraben, methyl paraben, sodium laurate, potassium laurate, castor oil, sodium myristate, potassium myristate, myristyl alcohol, cetyl alcohol, sodium palmitate, potassium palmitate, stearyl alcohol, fragrance, FD & C Red No. 4 (marketed as "Oil of Olay" by Olay Co., Inc., Wilton, CT 06897). The mixture was thixotropic. When diluted with a small amount of water, it gave a stable dispersion.

FORMULATION 3

Squid was collected in Delaware Bay, the pen cleaned of adventitious protein, dried and ground to 120 mesh (125 microns). This powder was used in the procedure of Formulation 1 in place of cuttlebone. A small amount of calamine-phenol was incorporated into the resulting salve.

FORMULATION 4

The procedure of Formulation 1 was repeated except that the commercial skin dressing contained water, mineral oil, coca butter, stearic acid, oat flour, cetyl alcohol, sodium lauryl sulfate, dimethicone, PEG-15 cocamine, triethanol amine, fragrance, Quaternium-15, carbomer-934, lanolin alcohol, propyl paraben, methyl paraben, stearic hydrazide, FD & C yellow No. 5, D. & C Red No. 19 (marketed as "Balm Barr" by Balm Barr, Inc., a subsidiary of the Mennen co., Morristown NJ 07960). The product was a smooth thick cream.

FORMULATION 5

A soft unguent is prepared by melting together 5 parts of cocoa butter, 4 parts of vegetable oil, 1 part of bacitracin ointment and dispersing therein 5 parts of finely powdered cuttlebone. The stirred mixture thickens as it cools and while still molten, it is transferred to appropriate containers. The prepared unguent was useful for treating hemorrhoids.

FORMULATION 6

The procedure of Formulation 1 was repeated except that the commercial skin dressing contained live yeast cell derivatives, supplying 2000 units Skin Respiratory Factor per ounce of ointment, shark liver oil (3%), and phenylemercuric nitrate 1:10,000 in a specially prepared rectal ointment base (marketed as "Preparation H" by Whitehall Laboratories, Inc., New York, NY 10017). The product speeds the healing of hemorrhoidal bleeding.

EXAMPLE 1

A man in his late 60's suffered each winter with the skin on the tip of his index finger and thumb cracking open and becoming sore. His doctor prescribed the use of "Synalar" Cream 0.025% (a cortico-steroid) twice a day. The cream made the fingers less sore and seemed to speed up the healing but did not prevent the skin from recracking.

When Formulation 1 was substituted, the effect was the same as with "Synalar". However, when the two agents were applied concurrently, the cracking cleared up and did not reappear.

EXAMPLE 2

A woman, age 73, received a first degree burn of about ¼ inch on a finger. The burn was white initially and there was no breakage of the skin. It was promptly treated with Mentholatum and then ice for about 20 minutes. Formulation 2 was then applied. An hour and a half later, the burn was sore and sensitive to warm water of dishwashing. Formulation 2 was again applied. Two hours later the burn was essentially cured. There was no pain from warm water. The burn spot was slightly wrinkled as if caloused, but one had to hunt for the spot, as it was not very evident.

EXAMPLE 3

A senior citizen (male, age 73) was exposed to the sun without a hat for 4-5 hours and appreciably sunburned on the forehead. The burn was treated with Mentholatum the same day, but this application was not very effective. The following day the burn was treated with Formulation 3. The day after that the soreness was gone on the treated area, but not back of the hairline, which had been missed with the preparation. This area was treated with Formulation 3 and within a day the soreness was completely gone.

EXAMPLE 4

A large spaniel dog had had a yeast burn on its leg that had been open for a year or so. It had been treated by a veterinarian by removal of the material (like proud flesh), along with shots, etc. However, the sore was not cured. Formulation 3 was applied and the leg bandaged. In a month the sore was essentially cured. The sore came back part way; it was red but not raw. The treatment with Formulation 3 was repeated and after 3 months the wound was cured.

EXAMPLE 5

A girl aged 13 was scratched by a cat on several fingers and knuckles, there were 6 scratches or skinned spots. There was bleeding and later, reddening, probably from an allergic reaction prevalent in her family. Formulation 1 was applied on the second day. The third day there was much less redness, no open bleeding and wounds were nearly cured. Formulation 4 was applied in continuing treatment. The fourth and fifth days, the scratches were still evident, but no longer bothered and some scabs were gone. Treatment continued. By the 7th day there were no scabs and no scars.

It is apparent that changes and modifications may be made without departing from the invention in its broader aspects. The aim of the appended claims, therefore, is to cover all such changes and modifications as fall within the true spirit and scope of the invention.

That which is claimed is:

1. A wound healing composition comprising an effective amount of finely divided cephalopod skeletons in a compatible topical carrier.

2. The wound healing composition of claim 1 wherein the cephalopod skeleton is cuttlebone.

3. The wound healing composition of claim 1 wherein the cephalopod skeleton is squid pen.

4. A process for facilitating healing of a wound in a mammal which comprises applying to said wound finely divided cephalopod skeleton.

5. The process according to claim 4 wherein the finely divided cephalopod skeleton is in a compatible carrier.

6. The process according to claim 4 wherein the finely divided cephalopod skeleton is cuttlebone.

7. The process according to claim 4 wherein the finely divided cephalopod skeleton is squid pen.

8. The process according to claim 4 wherein the finely divided cephalopod skeleton is in the form of a dust.

* * * * *